United States Patent [19]

Schwartz et al.

[11] Patent Number: 5,369,713
[45] Date of Patent: Nov. 29, 1994

[54] INSPECTION METHOD USING AREA OF INTEREST (AOI) ANALYSIS

[76] Inventors: Nira Schwartz; Arie Shahar; Richard Woods, all of 2800 Plaza Del Amo #187, Torrance, Calif. 90503

[21] Appl. No.: 82,437

[22] Filed: Jun. 28, 1993

Related U.S. Application Data

[63] Continuation of Ser. No. 911,130, Jul. 9, 1992, abandoned.

[51] Int. Cl.$^5$ .............................................. G06K 9/00
[52] U.S. Cl. ......................................... 382/8; 356/240; 348/86
[58] Field of Search ........................... 382/8; 356/240; 425/172, 140; 250/223 B; 358/101

[56] References Cited

U.S. PATENT DOCUMENTS

| | | | |
|---|---|---|---|
| 4,606,635 | 8/1986 | Miyazawa et al. | 358/106 |
| 4,608,709 | 8/1986 | Hedler et al. | 382/1 |
| 4,682,220 | 7/1987 | Beurskens | 358/106 |
| 4,691,231 | 9/1987 | Fitzmorris et al. | 358/106 |
| 4,914,289 | 4/1990 | Nguyen et al. | 250/223 B |
| 5,058,177 | 10/1991 | Chemaly | 382/8 |
| 5,095,204 | 3/1992 | Novini | 250/223 B |
| 5,171,979 | 12/1992 | Kwa et al. | 356/240 |
| 5,233,186 | 8/1993 | Ringlien | 250/223 B |

Primary Examiner—Jose L. Couso
Assistant Examiner—D. Richard Anderson
Attorney, Agent, or Firm—David Pressman

[57] ABSTRACT

A technique for detecting defects in stationary products or in products moving on a production line (102, FIG. 1) by analyzing area of interest (AOIs) of their modified images uses a matrix or linescan camera (104, FIG. 1) for taking images of products (102). The product's dimensions are measured with accuracy, and the existence and alignment of caps and seals is determined. The technique is much faster and more accurate than current techniques and is based up on an analysis of the AOIs and their discontinuities. (209 FIG. 1). Carefully selected AOIs of the modified image (2 to 8, FIG. 2) are saved in the memory of a computer (106, FIG. 1). The method also includes loading look-up tables to modify the gray levels of the products; saving AOIs in memory to be analyzed (FIG. 1); analyzing AOl data, counting pixel discontinuities, etc. The results can be used to measure product ovality, check caps and seals on products, and check changes of fluid or content levels in containers.

4 Claims, 3 Drawing Sheets

INSPECTION METHOD USING AREA OF INTEREST (AOI) ANALYSIS

This is a continuation of application Ser. No. 07/911,130, field on Jul. 9, 1992, which was abandoned upon the filing hereof.

BACKGROUND—CROSS REFERENCE TO RELATED APPLICATION

The invention of this application is related to that of our copending application entitled "Inspection method using unique template and histogram analysis", Ser. No. 07/706,800, Filed May 29, 1991 now U.S. Pat. No. 5,204,911.

Background—Field Of The Invention

Generally, the field of this invention relates to quality control, particularly to a machine for inspecting and measuring products moving on a production line. The products are accepted for use or rejected based up on the inspection results.

Background—Prior Art

Image processing systems are used a great deal in today's product quality control systems. Image processing systems are replacing human power since they have the advantages of higher throughput, better inspection accuracy and lower cost.

An inspection system contains a light source with a unique wavelength that illuminates the product being inspected. Images of the products inspected are stored in a computer's memory for analysis by means of an algorithm, which is also stored in the computer's memory.

Recently, the structure of products has became more complicated and harder to inspect. A preformed product 102 (FIG. 1) is the first stage of a full-sized plastic container. The ovality, that is the roundness of the preform, is measured in one inspection operation before the product is inserted into a glass or plastic blowing machine (not shown), in which it is expanded into a full-sized container.

The ovality measurement must be very accurate. If a preform's ovality is not within the desired accuracy, it must be rejected before entering the blowing machine. If an inferior preform does get into the blowing machine, it will break, causing damage to the machine and stopping the production line.

Another common inspection operation on a production line (after the preform is blown into a container, filled, and sealed or capped) is to detect the seal or cap on the top of a container. The position of the seal must be very accurate to prevent gas or liquid from leaking out of the container.

Today high speed, very accurate, and cost effective inspect-on machines are needed. An automated inspection machine analyzes images of complicated structures, such as preforms 102 (FIG. 1) and seats (caps) 204 (FIG. 2) which are positioned on the product. The images are taken by a video camera and stored in the memory of a computer. Several standards for image acquisition exist, depending on the type of the camera used. In the US the standard is known as RS170 which generates an image of 491 horizontal lines by 649 pixels per line. The acquisition rate is 3 images per second. There are non-standard cameras with higher rates of image acquisition, or line cameras that use line sensors with various numbers of pixels.

Complicated measurements of highly structured products, such as containers, need a line-by-line image algorithmic analysis. That requires a lot of processing time and results in low production line throughput.

OBJECTS AND ADVANTAGES

Accordingly, it is an object of the invention to provide an improved method for inspecting, measuring, and sorting products with highly complex structures to find defects that may be present in such products, while they are moving on a production line.

It is also an object to measure the ovality of products and to determine whether they are within a desired accuracy range, to measure deviations in the positions of products by using pixels as basic measuring elements, to evaluate dimensions of products, to determine defects jr, the products in terms of their dimensional accuracy, and to make such measurements using real-time computer techniques. Still further objects and measures of the invention will be apparent after consideration of an ensuing description and accompanying drawings.

Figure 1:
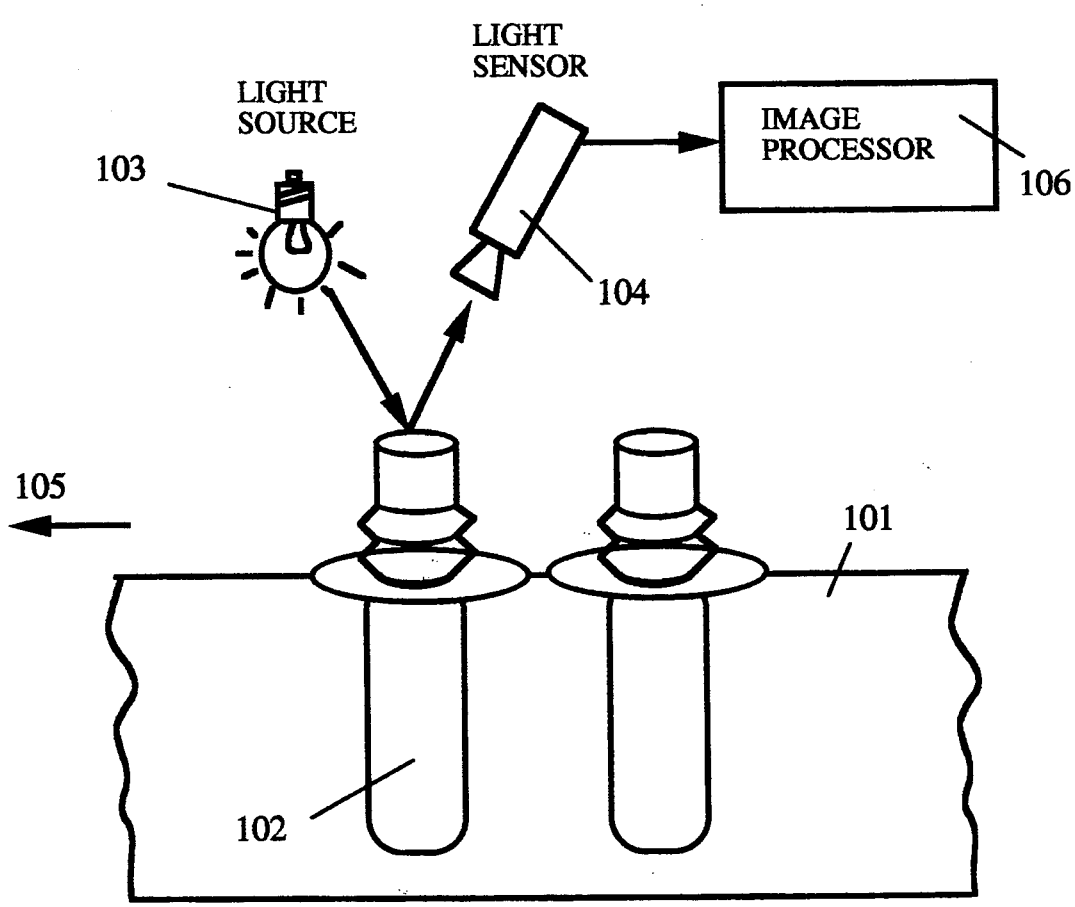
FIG. 1 is a schematic view of a quality-control system in accordance with the invention.

Reference Numbers
R1 Radius
R2 Radius
V1 Gray level value
V2 Gray level value
V3 Gray level value
V4 Gray level value
101 Conveyor
102 Product preform
103 Light source
104 Light sensor
105 Direction of motion
106 Image processor
201 Container
202 Image
203 Point on cap
204 Cap
205 Point on cap
206 Background
207 line
208 line
209 Horizontal AOl
210 Horizontal AOl
211 Horizontal AOl
212 Transition point
213 Transition point
214 Transition point
215 Transition point
216 Transition point
217 Transition point
218 Transition point
219 Transition point
220 Noise
221 Point on cap
223 Fluid level
224 Fluid level
225 Bar
226 Bar
227 AOl 228 AOI
229 Transition point
230 Transition point
301 Transition point
302 Transition point
303 Transition point
304 Transition point
305 Transition point
306 Transition point
307 Transition point
308 Dashed line
309 Dashed line
310 Background noise
311 Ring
312 Background level
313 Modified image
314 Transition point

GENERAL DESCRIPTION OF THE METHOD

The method of the invention consists of the following sequential steps:
1 A product is scanned to create an initial image of the product.
2 A modified product image is created by modifying the gray levels in the initial image.
3 The results are saved in memory.
4 Areas of interest (AOIs) within the modified image are created to match the product's dimensions and uncertainty of its position.
5 Data of the AOIs is analyzed by counting pixels, discontinuities, and transitions
7 Measurements are analyzed for statistical results.
Each of the above steps will now be considered separately in detail below.

Basic Terminology

Prior to discussing the present method the following definitions are presented to aid in understanding same.

Image format: This Indicates image size. The image format standard in the US is RS170, which means that an image is composed of 491 lines by 649 pixels. The image acquisition rate is 30 images per second.

Pixel: The smallest element of an image to be individually processed in a video display system. Therefore a pixel is the smallest division in any accuracy measurement.

Gray level: The full intensity that the camera is able to represent divided into 128 levels. Each pixel has an intensity that is a portion of the maximum intensity and is represented by a corresponding gray level.

LUT: A Look-Up Table, uses the digital data value of a pixel as an input or index into the table. Each input value has a corresponding output value. The output values are determined at the time the LUT is defined; all index values can map to a single value; groups of index values can also map to a single value. The choice is determined by the function which the user intends the LUT to serve.

FIG. 1 - Product Inspection System

FIG. 1 is a general schematic configuration of an entire system for carrying out an inspection operation according to the method of the invention. Product preforms (102) to be inspected move on a conveyor 101 in a direction 105. The preforms are illuminated by a light source 103, and their images are taken by a sensor 104, which is an industrial camera. The images are saved in memory, which is a part of an image processor 106, such as "Overlay Frame Grabber" (OFG) produced by Imaging Technology Inc., Woburn, MA.

Image processor 106 also includes a personal computer, preferably incorporating an 80486 microprocessor operating at 50 MHz. Images are stored in the memory of the OFG unit. Processor 106 also includes hardware lookup tables (not shown). These tables are used for modifying the image gray levels according to a pre-loaded conversion table. The table is loaded at the startup cycle of the processor or the algorithm. An example of a modifying table is: (1,11), (2,12), (3,13). That means all the original gray levels in table with values 1, 2, and 3 are shifted up by a value of 10. An example for a quantizing table is: (4,60), (5,60), (6,60). That means a set of original gray levels 4, 5, and 6 are converted to the value 60.

Processor 106 also contains a hardware board (not shown) which includes a microprocessor for calculating mathematical operations related to :he AOIs while they are saved in the memory. The motherboard of the processor unit includes on-board RAM. This board includes an algorithm for processing the AOIs in the modified product images. Hardware systems like these exist on the market today. They are manufactured by imaging technology Inc., supra.

Upon system power up, the algorithm stored in the processing unit creates AOIs that are saved in memory. Then the lookup tables are loaded with the modified values. At that stage the image processing unit is endlessly looping, while waiting to obtain a product image from light sensor 104. An image is sent to processor 106 when product 102 crosses light source 103. The lookup tables shift the gray levels of the product image to create a modified product image, before the saving in memory takes place. Processor 106 analyzes the AOIs of the image. The processor analyzes only the data related to the pre-defined AOIs, not any other data of the modified image. Finally the algorithm analyzes the product's dimensions to detect the defects.

Figure 2:
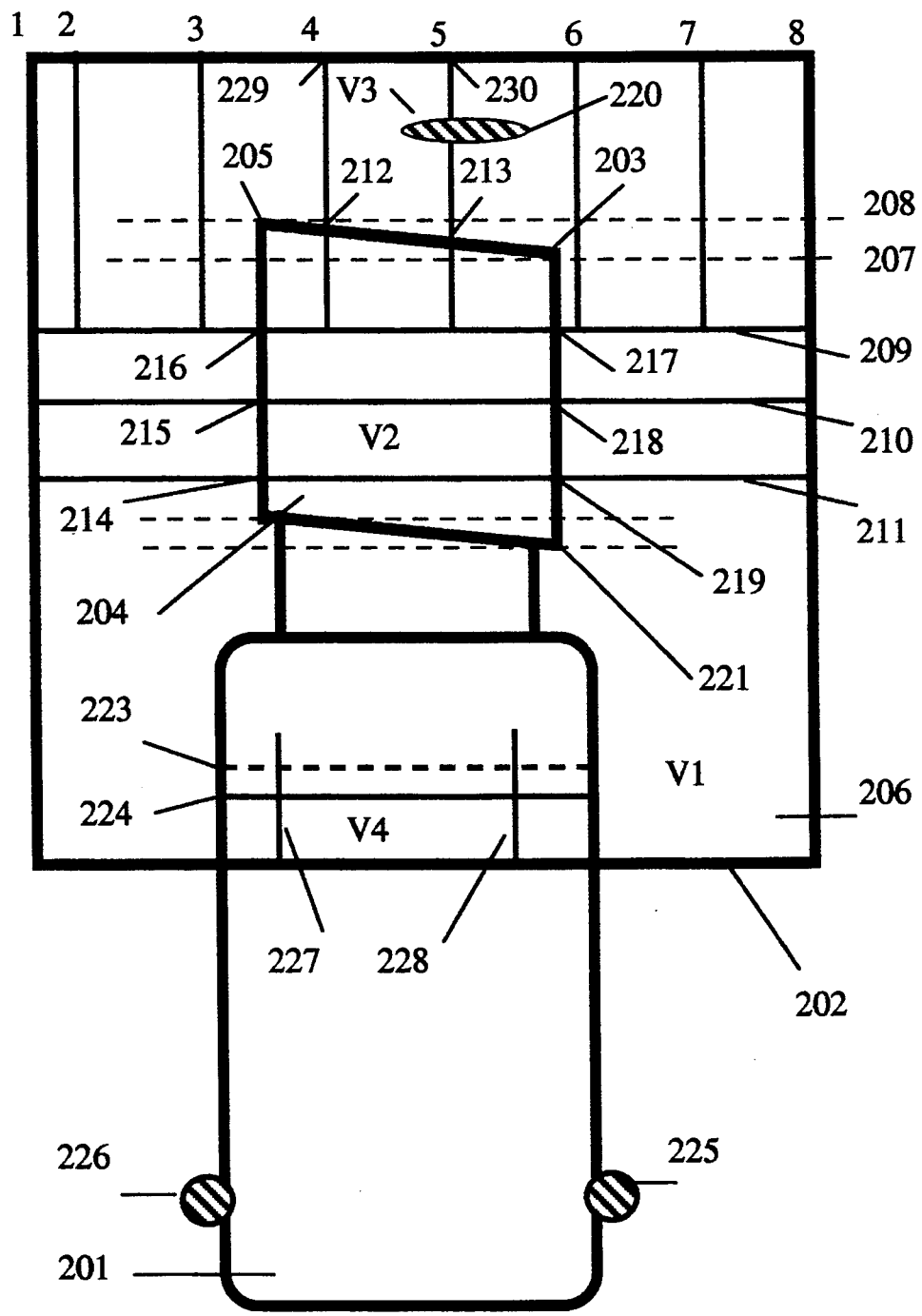
FIG. 2 is a diagram illustrating a capped container in accordance with the invention.

FIG. 2—Creation of AOIs On products Images

FIG. 2 shows, in accordance with the invention, a modified image 202 of the upper part of a container 201 taken by a camera. The container contains fluid up to level 224. The top of the product contains a cap 204. The product's background is shown at 206 with background "noise" 220, (Noise is a result of taking an image with a camera that has lenses with too deep a focal depth so that unwanted background is picked up in the image). The camera is aligned so it will scan image lines (not shown) which are parallel to fluid level 224, to a reference location on the product itself or to any fixed point in the background (not shown). The original product image (not shown) was modified by the use or the LUT. The result is plain background 206 with a gray level value V1, a cap 204 with a gray level value V2, background noise with gray level value V3, and the fluid in the container with gray level value V4. The width of the cap is the distance between points 205 and 203. The height of the cap is the distance between points 203 and 221.

A transition is defined whenever there is a change in the gray level values. For example, a change from gray level V1 to gray level V2 along vertical AOI 4 is defined as a transition and is shown at 212.

In the current example, the modified image has a standard numbers of lines, i.e., 512. Each line contains 512 pixels so that the image has 512 lines by 512 columns.

The vertical AOIs in the image are labeled 1, 2, 3, 4, 5, 6, 7, 8 on the top of the image, and 227 and 228 on the bottom of the image. The horizontal AOls in the image are labeled 209, 210, 211. In the current example, the size of each horizontal AOl (209, 210, and 211) is 1×512 pixels, i.e., one pixel width with a length of 512 pixels, or one standard image line. However other sizes are good as well. The vertical AOls numbered 2, 3, 4, 5, 6, 7, 227, and 228 are one pixel wide with a length that is less than a full line.

The product's vertical and horizontal positioning within the image is uncertain. Cap inspections require checking that a cap is present, or that it is aligned with fluid level 224, or to any reference on the product (not shown). This can be done by choosing the distance between two vertical AOls to be smaller than the width of the cap, and two horizontal AOls to be smaller than the height of the cap (as will be explained later). Distances between AOls are expressed in number of pixels.

The AOls in the images are designed very carefully to highlight points of interest on the product and to make it possible to determine the product'S dimensions and alignment without the necessity to analyze a full product image, or to have the product positioned to a predetermined point within the image.

E.g., assume that the product's position is uncertain within a distance that is larger than the dimension to be measured. This will require AOls spread apart by a distance that is less than the product's dimension. For example if the product's diameter is 22 mm, and the uncertainty in its position is 30 mm, then the distance between two line-AlOs should not be bigger than 22 mm. Such a distribution of AOls in the image area will assure that wherever the product's location is within the image, at least one of the AOls will have the data about the product's dimensions. A further example will be given shortly.

For another example, assume that the product's position is uncertain within a distance that is smaller than the dimension to be measured. This will require AOls spread apart by a distance that is less than the product's dimension and larger than the uncertainty distance. For example if the product's diameter is 22 mm, and the uncertainty in its position is 3 mm. then the distance between two AlOs should be smaller than 22 mm and larger than 3 mm. Such a distribution of AOls in the image area will assure that wherever the product's location is within the image, at least one of the AOls will have the data about the product's dimensions. A further example will be given shortly.

Since high-speed memory is costly, only the data of the AOls and not data of the full image are saved in the memory of image processor 106 (FIG. 1).

Inspecting cap existence:

Data analyses of AOls 209, 210, 211 can be used to determine if the cap is in place. The number of pixels with gray level V2 between transition points 216 to 217 along AOl 209 must be equal to the width of the cap. The procedure is repeated for AOl 210 with transition points 215 to 218 and for AOl 211 with transition points 214 to 219. A data match of the AOl within a predetermined accuracy indicates the existence of the cap. AOls 209, 210 and 211 were carefully designed to be able to inspect cap existence regardless of the horizontal displacement of the cap within the image. That means that the inspection method will still perform as long as the cap is within the image.

Inspecting seal alignment:

FIG. 2 shows a cap that is not aligned. The section between points 205 and 203 define the top of the cap and is not parallel to fluid level 224. Also the angle (not shown) between points 203, 205, and 208 does not equal zero.

The cap alignment can be measured by analyzing the data of AOls 4 and 5. The number of pixels with gray levels not equal to V2 within AOl 4 is N1 (not shown). N1 is the number of pixels between transitions 229 and 212 on AOl 4. The number of pixels with gray levels not equal to V2 within AOl 5 is N2 (not shown). N2 is the number of pixels between transitions 230 and 213 on AOl 5. Pixels with three different gray levels exist on AOl 5: background 206 with pixels having gray level V1, background noise 220 with pixels having gray level V3, and cap 204 with pixel having gray level V2. In the current example, value N2 will include the number of pixels with gray level V3 and V1. The distance between AOl 4 and AOl 5 along dashed line 208 is N3. The alignment angle between points 203, 205 and line 208 is derived from the following equation.

$$\text{Tan (angle)} = (N1-N2)/N3 \tag{1}$$

If the camera is not aligned with any reference position, the angle must not be zero. Its value can be compared to an angle derived from a standard container used as a reference.

Eq (1) cannot be solved when one of AOls 4 or 5, or both, do not include the gray levels of the cap's pixels. The value of N1 or N2 or both are unknown. This case (not shown) can happen when the cap's horizontal displacement is large. In that case only one of AOls 4 or 5 or none of them contain cap pixels with gray levels. To assure the accuracy of the inspection method perform for as long as the cap is within the image, additional AOls parallel to AOls 4 and 5 (not shown) must be included. The additional AOls must be separated by a distance that is less than the cap's width.

Inspection of gas pressure:

Gas will leak out of the container whenever the cap is not aligned satisfactory. Inspection of the amount of leakage from the container is measured indirectly. The container is first automatically pressed be:ween two bars 226 and 225 (FIG. 2) on the production line. Those bars will squeeze the container, causing the fluid level to rise from level 224 to a higher level 223. Before changing the volume of the container, the number of pixels with gray level V4 within AOl 227 is N4. After changing volume, the number of pixels with gray level V4 within AOl 227 is N5.

The pressure P is proportional to the difference between the two fluid levels, expressed in number of pixels. The dependency function H can be evaluated by statistical measurements over a group of satisfactory containers. The function itself can be stored in the memory of the computer to be used for the acceptance decision on the production line.

$$P = H(N5-N4) \tag{2}$$

Equation (2) can be repeated for AOl 228. The results obtained for AOts 227 and 228 can be averaged from the final result.

Figure 3:
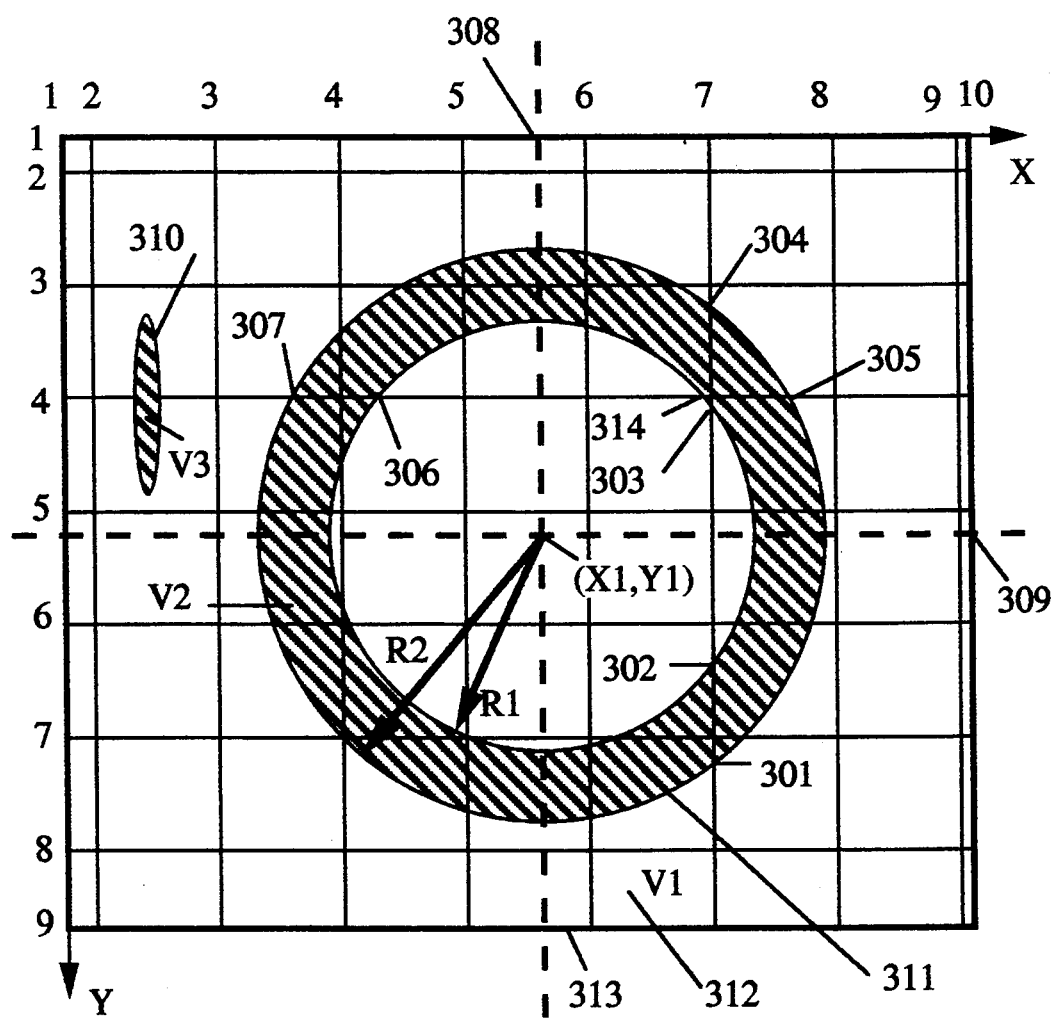
FIG. 3 is a diagram illustrating a top view of a preform in accordance with the invention.

FIG. 3—Quality measurement

FIG. 3 shows, in accordance with the invention, a modified image 313 and a top view of a preform product 102 FIG. 1 taken by a camera. The product's background is indicated at 312 with background noise 310.

The original product image (not shown) was modified using the LUT. The result is plain background 312 with a gray level value V1, a ring 311 with a gray level value V2 and background noise with gray level value V3.

A transition is defined whenever there is a change in the gray level values. For example, a change from gray level V1 to gray level V2 along vertical AO1 7 is defined as a transition and is shown as 301 and 303.

In the current example, the modified image has a standard numbers of lines and columns, i.e., 512×512. (Each line contains 512 pixels.)

The vertical AOls in the image are labeled 1 to 10 on the abscissa, or X axis, and horizontal AOls 1 to 9 on the ordinate, or Y axis. In the current example, the size of each horizontal or vertical AO1 is 1×512 pixels, i.e., one pixel width with a length of 512 pixels, or one standard image line. However other sizes are acceptable.

The vertical and horizontal positioning of the product within the image is uncertain. Quality inspections require checking deviation from a perfect circle. The quality of ring 311 is to be inspected, and also the internal and external radii R1 and R2, respectively. This can be done by choosing the distance between two vertical (or two horizontal) AOls to be smaller than the inner diameter (as will be explained later). Distances between AOlS are expressed in numbers of pixels.

The AOls in the images are designed to very carefully highlight points of interest on the product. They make it possible to determine the product's dimensions and alignment without the necessity to analyze a full product image, without the necessity to have the product positioned at a predetermined point within the image, and without the necessity so store the full image in the memory. For example only two AOls are needed to come up with the diameters of a ring displayed inside an image. The first AO1 is one standard image line, and the second AO1 is one standard column. The first and second AOls are spaced away from the abscissa and the ordinate respectively, to create chords in the ring. Uncertainty in the ring's position within the image should influence which line number or column in the image chosen as AOls while still being able to create two chords. The following example will explain this in detail.

Inspecting Preform Quality—Inner Radius:

Data analysis of vertical AO1 7 and horizontal AO1 4 can be used to determine if the preform ovality is acceptable, i.e., the size of R1 must be within predetermined accuracy. On AO1 7, the number of pixels from ordinate X to transition point 303 is N6. The number of pixels from ordinate X to the transition point 302 is N7. By simple trigonometry, the equation to define the dashed line 309, which represents a chord within a circle, is:

$$Y1 = (N6+N7)/2 \qquad (3)$$

This is also the equation for the diameter of the preform.

The mathmatical equation describing line 309 is also the equation describing the diameter. The procedure is repeated for horizontal AO1.4. The number of pixels from ordinate Y to transition point 306 is N8. The number of pixels from ordinate Y to transition point 314 is N9. By simple trigonometry, the equation to define dashed line 308, which represents a chord within a circle, is:

$$X1 = (N8+N9)/2 \qquad (4)$$

This is also the equation for the diameter of the preform.

The pair (X1,Y1) defines the center of the inner circle with radius R1.

That calculation is repeated for another pair of AOls, e.g., vertical AO1 7 and horizontal AO1 6 and is resolved with (X2,Y2) (not shown) as a possible center for the inner circle. As long as the two inner circle center results are within the desired accuracy, the preform is accepted for use or for additional inspection.

The calculation can be repeated for many other pairs of AOls. Averaging of those results should be done when fluctuations in the intensity/of light source 103 (FIG. 1) are expected over a period of time.

Inspecting Preform Ovality—Outer Radius:

Data analyses of vertical AO1 7 and horizontal AO1 4 can be used to determine if the preform's ovality is acceptable, i.e., the size of R2 must be within a predetermined accuracy. The number of pixels from abscissa X to transition point 304 is N10. The number of pixels from ordinate X to transition point 301 is N11. By simple trigonometry the equation to define dashed line 309, which represents a chord within a circle, $$Y3 = (N10+N11)/2 \qquad (5)$$

This is also the equation for the diameter of the preform.

Dashed line 309 is also a diameter. The procedure is repeated for horizontal AO1 4. The number of pixels from ordinate Y to transition point 307 is N12. The number of pixels from ordinate Y to transition point 305 is N13. By simple trigonometry the equation to define dashed line 308, which represents a chord within a circle, is:

$$X3 = (N12+N13)/2 \qquad (6)$$

This is also the equation for the diameter.

The pair (X3,Y3, not shown) defines the center of the outer circle with radius R2.

The calculation is repeated for another pair of AO1, e.g., vertical AO1 7 and horizontal AO1 6 and is resolved to X4, Y4 (not shown) as a possible center for the inner circle. As long as the two results are within the desired accuracy, the preform is accepted for use or for additional inspection.

Background noise 310 is eliminated by evaluating its width in pixels and comparing it to the difference (R2-R1). If this continues to be an uncertain case for calculating the center of the circle, then the noise distance to the next transition is calculated and compared with the estimated chord length expected in the region of the valid AO1. If the data is still confused, then the current AO1 should be neglected and the next one in line should be selected for calculation, e.g., AO1 4 will be replaced by AO1 6.

The accuracy of measurement can be increased by the use of a linescan camera. The image of a linescan camera is only one line a thousand pixels long. The size of the AO1 can be full line or a part of a line. An application is the use of two or more (not shown) linescan cameras for calculating the preform's ovality. One linescan camera's output can be represented as vertical AO1 7, and the other linescan camera's output can be represented as AOl 4. The linescan cameras do not need to be aligned perpendicular to each other since each one will represent a chord in the inner or outer circle of the preform.

Measurements of quality control can be applied in the automobile industry to measure ovality of pistons or other car parts (not shown) or relative positions of moving parts at high speed. Ammunition (not shown) represents another area where parts move with high speed and require a fast inspection method.

SUMMARY, RAMIFICATIONS, AND SCOPE

Accordingly, the reader will see that we have provided a technique that can measure the ovality of static or moving products, having a size equivalent to one pixel or more, by analyzing selected AOIs. This technique enables us to measure, with great accuracy, a moving product's dimensions and therefore fluctuations in such dimensions. This technique also enables us to detect the presence of caps and seals on products. The technique is much faster than previous methods. AOls of images are a primary part of the technique and their shapes and separation distances are carefully selected and stored in the memory of the computer for use in real time. Careful modifying and quantizing of the image's gray levels is essential to provide satisfactory results when analyzing data of the AOl's pixels.

While the above description contains many specific details, these should not be construed as limitations on the scope of the invention, but as exemplification's of the presently preferred embodiments thereof. Many other ramifications and variations are possible within the teachings to the invention.

Therefore, the scope of the invention should be determined, not only by examples given, but by the appended claims and their legal equivalents

We claim

1. A method for inspecting a container that is partially filled with a fluid having a surface level, which may have defects, and which moves on a production line in a predetermined direction, comprising:
   squeezing said container with a predetermined force to change the surface level of said fluid,
   providing a light source which is arranged to shine light upon a finish of said container, including the surface level of said fluid, so that said light is reflected from said finish of said container along a return path,
   providing a sensor in said return path to collect light reflected from said finish of said container,
   providing a processing unit with a memory,
   creating a container image of said finish by using said sensor to sense reflected light from the finish of said container, said sensor being arranged to produce an electrical signal representative of a reflected product image of said finish, said container image comprising a multiplicity of pixels with intensity levels expressed as respective gray levels,
   modifying said container image in said processing unit to produce a modified container image by modifying said gray levels of said container image to highlight transition points of said container image,
   providing and saving in said memory of said processing unit a plurality of computer-generated artificial areas of interest of said modified container image, said plurality of computer generated artificial areas of interest representing separate areas of said container which are separated by a plurality of pixels, all of said pixels of said plurality of computer generated artificial areas of interest together being less than the number of pixels of which represent said container image, at least one of said plurality of computer generated artificial areas of interest including the gray levels of only some of said container's pixels, regardless of any uncertainty in said container's position in said given direction,
   analyzing said transition points in said plurality of computer generated artificial areas of interest, and
   utilizing said plurality of computer generated artificial areas of interest of said modified container image for product inspection.

2. The method of claim 1 further including making container images of said finish of said container, including the surface level of said fluid, before and after said squeezing.

3. A method for inspecting a sealed container that has been partially filled with a fluid having a surface level, which may have defects, and which moves on a production line in a predetermined direction, comprising:
   applying a force to said container to cause the level of said fluid to rise inside said container, providing a light source which is arranged to shine light upon a finish of said container, including the surface level of said fluid, so that said light is reflected from said finish of said container along a return path,
   providing a sensor in said return path to collect light reflected from said finish of said container,
   providing a processing unit with a memory,
   creating a container image of said finish by using said sensor to sense reflected light from the finish of said container, said sensor being arranged to produce an electrical signal representative of a reflected product image of said finish, said container image comprising a multiplicity of pixels with intensity levels expressed as respective gray levels,
   modifying said container image in said processing unit to produce a modified container image by modifying said gray levels of said container image to highlight transition points of said container image,
   providing and saving in said memory of said processing unit a plurality of computer-generated artificial areas of interest of said modified container image, said plurality of computer generated artificial areas of interest representing separate areas of said container which are separated by a plurality of pixels, all of said pixels of said plurality of computer generated artificial areas of interest together being less than the number of pixels of which represent said container image, at least one of said plurality of computer generated artificial areas of interest including the gray levels of only some of said container's pixels, regardless of any uncertainty in said container's position in said given direction,
   analyzing said transition points in said plurality of computer generated artificial areas of interest, and
   utilizing said plurality of computer generated artificial areas of interest of said modified container image for product inspection.

4. The method of claim 3 wherein said container is squeezed to cause the level of said fluid therein to rise.

* * * * *

UNITED STATES PATENT AND TRADEMARK OFFICE
CERTIFICATE OF CORRECTION

PATENT NO.: 5,369,713
DATED: November 29, 1994
PATENTEES: Nira Schwartz et al.

It is certified that error appears in the above-identified patent and that said Letters Patent is hereby corrected as shown below:

Col.1, line 6, change "field" to —filed—.

Col.1, line 56, change "inspect-on" to —inspection—.

Col.3, line 50, change "Table," to —Table—.

Col.5, line 20, change "product'S" to —product's—.

Col.8, line 45, change "AOI" to —AOIs—.

Signed and Sealed this

Twenty-first Day of February, 1995

Attest:

BRUCE LEHMAN

Attesting Officer     Commissioner of Patents and Trademarks